United States Patent [19]

Mertsch

[11] Patent Number: 5,529,687
[45] Date of Patent: Jun. 25, 1996

[54] FILLING SLUICE FOR APPLIANCES FOR THE TREATMENT OF INFECTIOUS WASTE

[75] Inventor: Joachim Mertsch, Nienhagen, Germany

[73] Assignee: Sanitec, Inc., West Caldwell, N.J.

[21] Appl. No.: 512,344

[22] Filed: Aug. 8, 1995

Related U.S. Application Data

[63] Continuation of Ser. No. 276,871, Jul. 18, 1994, abandoned, which is a continuation of Ser. No. 983,858, filed as PCT/US91/05735, Aug. 12, 1991, abandoned.

[30] Foreign Application Priority Data

Sep. 5, 1990 [DE] Germany .......................... 40 28 101.9

[51] Int. Cl.⁶ .................................................. B01D 11/04
[52] U.S. Cl. ............................................ 210/205; 210/450
[58] Field of Search .................................. 210/205, 218, 210/450, 472; 422/296, 300, 302, 303

[56] References Cited

U.S. PATENT DOCUMENTS 4,356,012  10/1982  Hofstetter .
4,374,491  2/1983   Stortroen et al. .
4,934,392  6/1990   Henfrey .
5,048,766  9/1991   Gaylor et al. .

FOREIGN PATENT DOCUMENTS 1-144040  10/1989  Japan .

OTHER PUBLICATIONS

International Search Report No. PCT/US91/05735 completed Sep. 20, 1991, mailed Oct. 24, 1991.
PCT Notification of Transmittal of Int'l Preliminary Exam. Report mailed Dec. 14, 1992.
Notice of Reasons for Rejection mailed Jan. 11, 1994 (Japanese Counterpart) (Translation).

*Primary Examiner*—Frank Spear
*Attorney, Agent, or Firm*—Wigman, Cohen, Leitner & Myers

[57] ABSTRACT

The invention relates to a filling sluice for appliances for the treatment of infectious waste, with at least two chambers separable from on another via a rotary vane of stationary mounting and located in a sluice housing closable in a fluid-tight manner relative to the outside. For the rapid and reliable sluicing of infectious waste without a release of infectious germs, the rotary vane is arranged as a swingable partition wall between axially adjacent chambers and can be brought via an inflatable continuous sealing element to bear in a sealingly closing manner on the inner wall of the sluice housing.

6 Claims, 2 Drawing Sheets

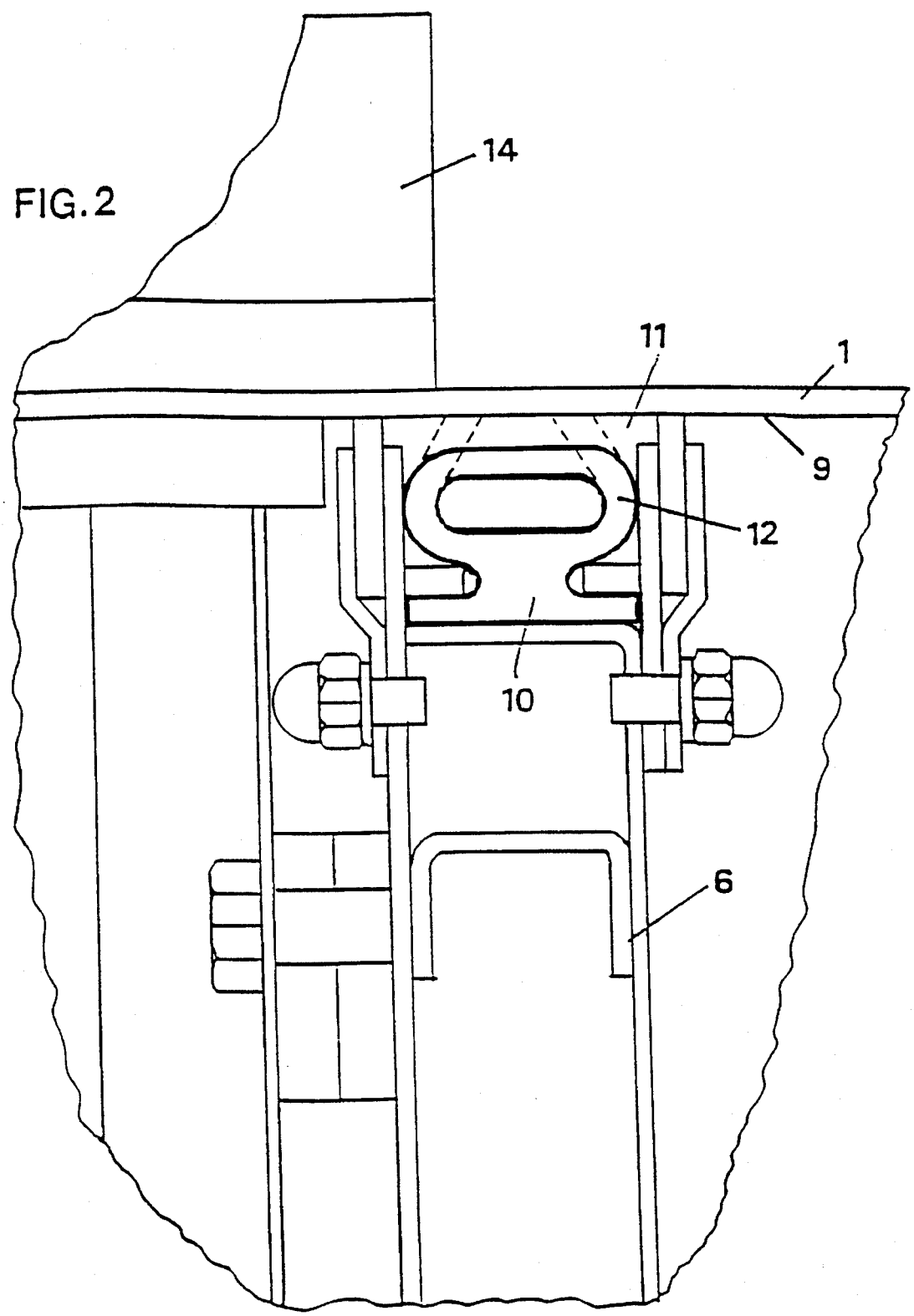

FILLING SLUICE FOR APPLIANCES FOR THE TREATMENT OF INFECTIOUS WASTE

This is a continuation of application Ser. No. 08/276,871, filed on Jul. 18, 1994, now abandoned, which is a continuation of application Ser. No. 983,858, filed as PCT/US91/05735, Aug. 12, 1991, now abandoned.

The invention relates to a filling sluice for the treatment of infectious waste.

A filling sluice of the type mentioned is known from German Patent Specification 39 12 751. Arranged centrally in an essentially cylindrical hollow body having a funnel-shaped outlet portion at its bottom is a sluice wheel with three sluice vanes extending outwards at a respective angle of 120°. The sluice vanes subdivide the interior of the hollow body into three chambers separated from one another, which revolve during the rotation of the sluice wheel and which successively form an infeed station, transfer station and a disinfection station. This is intended to ensure that the infeed portion to be filled repeatedly in an appliance for the treatment of infectious waste does not release any infectious germs.

An essential disadvantage of the known filling sluice is that only small quantities of infectious waste can be sluiced. A multiplicity of sluice operations for filling a thermal treatment portion are therefore necessary. Another disadvantage is that the travel of the chambers in the sluice housing requires an independent disinfection station to be interposed this involving a high outlay in terms of construction and attendance.

An object of the invention is, therefore, to provide a filling sluice which allows rapid and reliable sluicing of infectious waste without a release of infectious germs.

This object is achieved according to claim 1.

This provides a filling sluice which is designed with stationary sluice chambers and which allows a reliable and economical sluicing of infectious waste merely by means of a rotatable version of a partition wall common to the chambers in conjunction with a special sealing element. At the same time, the partition wall performs not only a sealing function between axially adjacent chamber regions, but also a transporting function of conveying the infectious waste of any one chamber into the other chamber.

Preferably, a rotary vane is arranged between two chambers which define a filling section and a delivery section of a compact disinfection or sterilisation unit. The filling section can be formed by a chamber of semicylindrical shape, the content of which is emptied into the chamber of the delivery section during a forward and/or backward movement of the rotary vane through at least approximately 180°. This design of the filling sluice allows large dimensions of the sluice housing, with the result that high throughput quantities can be moved during one sluice operation. Furthermore, a disinfection of the sluice chambers consisting of only a few parts can be carried out reliably by means of steam, water and/or other solutions. A repeated opening of the filling sluice for the introduction of infectious waste, with subsequent treatment, for example in a disinfection or sterilisation unit, therefore takes place without the risk that infectious germs will be released.

An inflatable sealing element guarantees a wear resistant sealing closure by the rotary vane, the sealing function being achieved even without an exact adjustment of the position of the rotary vane. A desirable expand-ability of the sealing element can be obtained by designing the sealing element with a tubular extension. Because the sluice chambers are subjected to steam, the sealing element preferably consists of a heat-resistant plastic.

A simple constructive design of the rotary vane can be obtained by mounting this on a vertical mid-axis. The rotary vane can then consist of two vane blades of symmetrical design. The assembly and maintenance can be simplified by the use of a two-part drive shaft consisting of an upper and a lower shaft.

Further embodiments of the invention are to be taken from the following description and the appended claims.

The invention is explained in more detail below by means of the preferred embodiment illustrated in the accompanying figures.

FIG. 2 shows a cutout from FIG. 1 enlarged and in detail;

Figure 4:
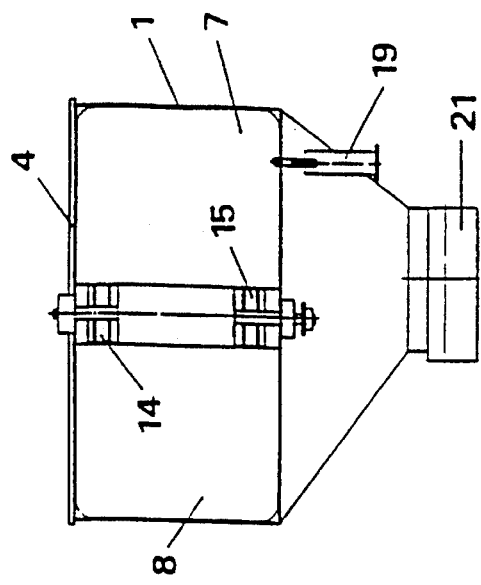
FIG. 4 shows a cross-section view of the filling sluice according to FIG. 1.
Figure 1:
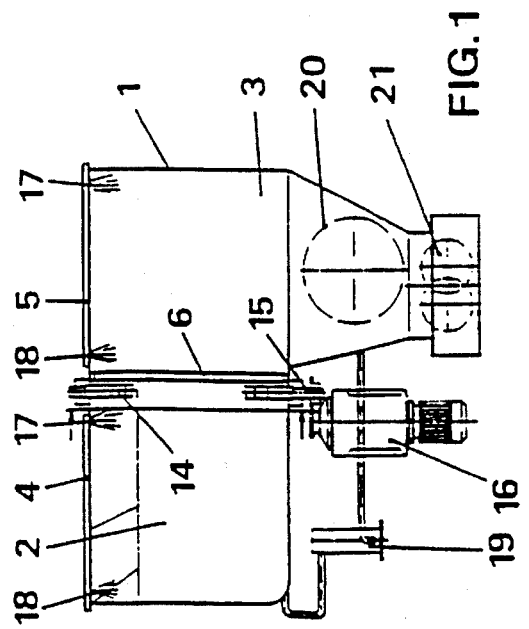
FIG. 1 shows a longitudinal section through a filling sluice.

FIG. 1 shows a filling sluice with a sluice housing 1, in which are arranged two laterally adjacent chamber sections separable from one another via a sealingly closing partition wall. In the preferred embodiment illustrated, the two chamber sections are formed by a filling chamber 2 and a delivery chamber 3. The two chambers 2, 3 are trough-shaped and are each sealingly closable relative to the outside via a cover 4, 5. The sealingly closing partition wall is formed by a rotary vane 6 which is mounted rotatably about a vertical mid-axis. The rotary vane 6 comprises two vane blades 7, 8 (see FIG. 4) spanning a separation surface, the outer circumferential line of which extends as far as the inner wall 9 of the sluice housing 1 in the area of the parting plane between the filling chamber 2 and delivery chamber 3.

As can be seen especially from FIG. 2, the rotary vane 6 carries a continuous sealing element 10 which is inflatable in order to ensure a temporary sealingly closing bearing of the rotary vane 6 against the inner wall 9. To receive the sealing element 10, the rotary vane 6 has a continuous edge slot 11, into which the sealing element 10 is laid. The sealing element 10 comprises an outwardly directed tubular extension 12 which experiences a change of shape during inflation, with the result that the sealing element 10 is pressed against the inner wall 9. The change of shape is illustrated by an extension 12 shown in broken lines in FIG. 2. Heat-resistant plastic is preferably provided as the material for the sealing element 10.

Figure 3:
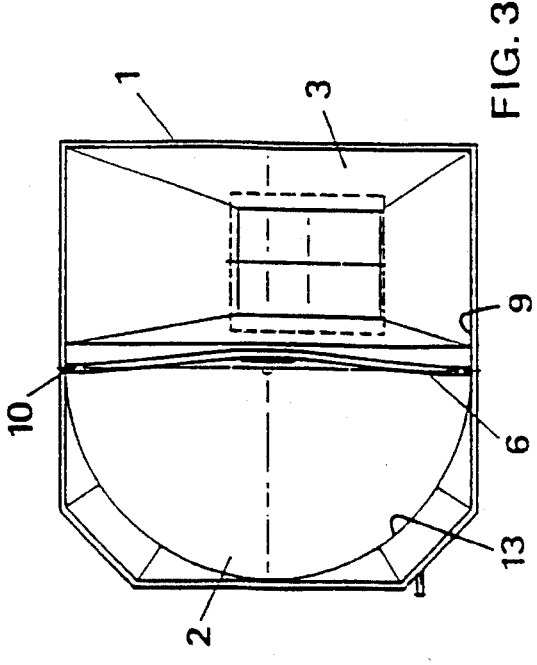
FIG. 3 shows a top view of the filling sluice according to FIG. 1.

In addition to the closing position of the rotary vane 6 shown in FIGS. 1 and 3, the latter can be rotated forwards and/or backwards through at least approximately 180°. The sluice housing 1 is made semi-cylindrical for the filling chamber 2, specifically with a size and curvature matched to the pivoting circle 13 of the rotary vane 6. The rotary vane 6 can consequently move through the filling chamber 2 and empty the waste introduced there into the delivery chamber 3.

To execute the rotational movement, the rotary vane 6 is coupled to an upper shaft 14 and a lower shaft 15. The shaft stem affords the possibility of mounting manual, electrical, hydraulic or pneumatic drive elements 16. For simple assembly and maintenance, the rotary vane 6 is fastened to the shafts 14, 15 with couple eccentricity in the axial direction and is equipped with slightly angle vane blades 7, 8 (see FIG. 3).

Each chamber has nozzles 17, 18 for flushing out the chambers 2, 3 with water and/or for admitting them to steam. If appropriate, solutions assisting disinfection can also be sprayed in. The nozzles 18 for the jets of water or solution are preferably designed as flat jet nozzles and are directed to the rotary vane 6 in the delivery chamber 2. Both chambers 2, 3 are connected to a condensate outflow 19 for discharging the steam and water introduced by the nozzles.

The shape of the delivery chamber 3 need be matched to the rotary vane 6 only to the extend that it is possible for the rotary vane 6 to swing between the closing positions. The delivery chamber 3 serves as a store for collecting the sluiced-in waste in order to transfer it to a treatment portion of a following appliance. For this, the delivery chamber is made funnel-shaped at the bottom and is equipped with a reciprocating feeder 20. The filling sluice can form the infeed portion of a compact disinfection or sterilisation unit, in which the infectious waste is treated thermally along a conveyor zone. If a prior comminution of the waste is necessary for this treatment, a comminuting device 21 can be connected directly to the bottom of the delivery chamber 3. Furthermore, the delivery chamber 3 can be connected to the atmosphere via a membrane-filter element.

The sluice housing 1 preferably consists of high-grade steel and can be made heatable.

The sluice operation with the filling sluice described above can be carried out as follows;

The rotary vane 6 is brought into the closing position, and a sealed-off separation between the filling chamber 2 and delivery chamber 3 is obtained by inflating the sealing element 10. The filling chamber 2 is cleaned and disinfected via the injection points 17, 18. The cover 4 of the filling chamber 2 is thereafter opened and the infectious waste introduced. After this infeed has ended, the cover 4 is closed and the air bled from the sealing element 10, with the result that the sealingly closing engagement of the rotary vane 6 with the inner wall 9 of the sluice housing 1 comes loose. The rotary vane 6 is then rotated forwards or backwards, during which the vane blade 7 or 8 rotating into the filling chamber 2 pushes the introduced waste in front of it and throws it into the delivery chamber 3 opened as a result of the rotational movement of the rotary vane 6. After a rotation of approximately 180°, the rotary vane 6 is in the closing position on the opposite side. The sealing element 10 is thereupon inflated, in order once again to obtain a sealingly closing separation of the emptied filling chamber 2 from the delivery chamber 3. The filling chamber 2 is then cleaned and disinfected again. Before every sluicing operation, the side of the rotary vane 6 facing the delivery chamber 3 is cleaned. The filling chamber 2 can then be filled again and further sluice operations carried out accordingly.

The actuation of the filling sluice is independent of the further treatment of the waste. Only the sluiced-in quantities need be matched to the receiving capacity of the intermediate store formed by the delivery chamber 3.

Although the invention has been described in connection with what is presently considered to be the most practical and preferred embodiment, it is to be understood that the invention is not limited to the disclosed embodiments, but rather, is intended to cover various modifications and equivalent arrangements included within the spirit and scope of the appended claims.

I claim:

1. An infectious waste filling sluice comprising:
   a. a first chamber comprising a vertically oriented half-cylinder forming a semicircular side wall and a generally planar side wall, said first chamber including an opening in the top thereof for loading infectious waste and means for sealing said top opening;
   b. a second chamber attached to said first chamber horizontally adjacent to said planar side wall of said first chamber, said second chamber including an opening in the bottom thereof for discharging infectious waste;
   c. an opening in said planar side wall of said first chamber forming a passageway between said first and second chambers;
   d. a rotary vane mounted on a vertical shaft in said opening in said planar side wall for rotary movement through at least 180°, said rotary vane having two blades and forming a partition in said opening between said first and second chambers when aligned with said planar side wall; and
   e. means for rotating said rotary vane through 180° and sweeping one of said blades through said first chamber and forcing infectious waste from said first chamber into said second chamber.

2. Apparatus as recited in claim 1 and further including an inflatable sealing member around the periphery of said vane adapted to seal around said opening in said planar wall to form a seal between said first and second chambers.

3. Apparatus as recited in claim 2 wherein said inflatable sealing member is contained in a continuous slot around the periphery of said rotary vane.

4. Apparatus as recited in claim 2 wherein said inflatable sealing member comprises a heat-resistant plastic.

5. Apparatus as recited in claim 1 wherein said first and second chambers include means for injecting steam and/or water and further including a condensate overflow.

6. Apparatus as recited in claim 5 wherein said first and second chambers each have at least one of said injecting means directed at said rotary vane.

* * * * *